United States Patent [19]

Burck et al.

[11] Patent Number: 5,272,076
[45] Date of Patent: Dec. 21, 1993

[54] COMPOUNDS AND METHODS FOR TREATMENT OF THROMBOEMBOLIC DISORDERS USING AN ADDUCT OF T-PA

[75] Inventors: Philip J. Burck; Ronald E. Zimmerman, both of Indianapolis, Ind.

[73] Assignee: Eli Lilly and Company, Indianapolis, Ind.

[21] Appl. No.: 714,537

[22] Filed: Jun. 13, 1991

[51] Int. Cl.$^5$ .................... C12N 9/96; C12N 9/48; C12N 9/70; A61K 37/547
[52] U.S. Cl. .................... 435/188; 435/212; 435/216; 435/219; 424/94.1; 424/94.64
[58] Field of Search .................... 424/94.64, 94.1; 435/212, 216, 219, 226, 188

[56] References Cited

U.S. PATENT DOCUMENTS

| | | | |
|---|---|---|---|
| 4,640,835 | 2/1987 | Shimizu et al. | 435/188 |
| 4,929,560 | 5/1990 | Edmunds et al. | 435/212 |

FOREIGN PATENT DOCUMENTS

| | | | |
|---|---|---|---|
| 0155388 | 9/1985 | European Pat. Off. | 435/188 |
| 0184363 | 6/1986 | European Pat. Off. | 435/188 |
| 0211592 | 2/1987 | European Pat. Off. | |
| 0419252 | 3/1991 | European Pat. Off. | |

OTHER PUBLICATIONS

Sarmientos, et al., "Synthesis & Purification of Active Human Tissue Plasminogen Activator From *Escherichia coli*:", Bio/Technology, vol. 7, May. 1989, pp. 495–501.
Burck et al., 1990, J. Biological Chemistry 265:5170.
Jackson et al., 1990, Circulation 82(3):930–940.
Wilhelm et al., 1990, Thrombosis and Haemostasis 63(3):464–471.
Higgins et al., 1990, Annu. Rev. Pharmacol. Toxicol. 30:91–121.

*Primary Examiner*—Douglas W. Robinson
*Assistant Examiner*—Kristin Larson
*Attorney, Agent, or Firm*—Thomas G. Plant; Leroy Whitaker

[57] ABSTRACT

The present invention provides adducts of human t-PA derivatives, which comprise a t-PA derivative that lacks the Finger, Growth Factor and Kringle 1 domains, bound to an amphipathic molecule. The invention also provides methods for preparing the adducts and compositions for the treatment of thromboembolic disorders.

39 Claims, No Drawings

L
COMPOUNDS AND METHODS FOR TREATMENT OF THROMBOEMBOLIC DISORDERS USING AN ADDUCT OF T-PA

FIELD OF INVENTION

The present invention provides an adduct of a human t-PA derivative, wherein said adduct comprises a t-PA derivative that lacks the Finger, Growth Factor and Kringle 1 domains, bound to an amphipathic molecule. The invention also provides methods and compositions for the treatment of thromboembolic disorders.

BACKGROUND OF THE INVENTION

Plasminogen activators are a unique class of enzymes that convert the catalytically inactive zymogen plasminogen to its active enzymatic form, plasmin. Plasmin is a Serine Protease requisite for the dissolution of fibrin (Colleen, D., 1980, *Thromb. Haemostasis* 43:77–89). Several plasminogen activators are now being used as in vivo fibrinolytic agents in the treatment of acute myocardial infarction (Tiefenbrunn, et al., 1989, *Fibrinolysis* 3:1–15). Tissue plasminogen activator (t-PA) has been the focus of considerable attention because its ability to activate plasminogen is significantly enhanced in the presence of fibrin (Rijken et al., 1982, *J. Biol. Chem.* 257:1920-2925), a property that should make it more clot specific when used as an in vivo fibrinolytic agent.

Based on the cDNA sequence of t-PA, the inferred sequence of 527 amino acids comprises five distinct structural domains: a Finger domain; a Growth Factor domain; two Kringle domains; and a Serine Protease domain (Pennica et al., 1983, *Nature* 301:214, and Banyai et al., 1983, *FEBS Lett.* 163:37–41). A series of deletion mutants of t-PA that comprise the Serine Protease domain and one or more of the other four structural domains of the intact molecule have been constructed (van Zonneveld et al., 1986, *Proc. Natl. Acad. Sci.* 83:4670; Erlich et al., 1987, *Fibrinolysis* 1:75–81; Haigwood et al., 1989, *Protein Engineering* 2:611–620; Higgins and Bennett, 1990, *Annu. Rev. Pharmacol. Toxicol.* 30:91). A t-PA derivative lacking the Finger, Growth Factor and Kringle 1 domains has been described by Burck et al., 1990, *J. Biol. Chem.* 265(9):5170-5177). This derivative, called mt-PA6, was constructed by deletion of the DNA encoding amino acids 4-175 of human t-PA (t-PA). mt PA6 produced by recombinant DNA techniques was found to possess greater fibrinolytic activity and a greater ability to activate thrombus-bound plasminogen than t-PA (Jackson et al., 1990, *Circulation* 82:930-940).

mt-PA6 is found in two glycosylation forms when produced by eukaryotic cell culture using recombinant DNA techniques. These two glycosylation forms account for the doublet of 40 and 42 kD bands seen when the purified mt-PA6 molecule is analyzed by gel electrophoresis. One of the glycosylation forms, Primary mt-PA6 (mt-PA6-P), is glycosylated at amino acid 276 (equivalent to amino acid 448 of t-PA) but not at amino acid 12 (equivalent to amino acid 184 of t-PA). The second glycosylation form, Variant mt-PA6 (mt-PA6-V), is glycosylated at both amino acids 12 and 276. mt-PA6 lacks the Kringle 1 domain and, therefore, lacks the glycosylation site at amino acid 117 of this domain. mt-PA6-V comprises 10-25% of the mt-PA6 molecules secreted from the Syrian hamster cell line AV12-664 (Burck et al., supra).

The thrombolytic potential of mt-PA6-V and its role in fibrinogen degradation and plasminogen degradation were examined using methods described by Jackson et al., supra. These studies demonstrated that diglycosylated t-PA derivatives lacking the Finger, Growth Factor and Kringle 1 domains, such as mt PA6-V, provide advantages over their partially glycosylated counterparts in the treatment of thromboembolic disorders. Although the monoglycosylated mt-PA6-P has a higher in vitro specific activity, the diglycosylated mt-PA6-V is a more efficient thrombolytic agent in vivo. mt-PA6-V displays the unexpected and advantageous properties of causing less systemic conversion of plasminogen to plasmin, is markedly less prone to metabolism to its two-chain form, and has a higher fibrinolytic versus fibrinogenolytic ratio than mt-PA6-P. Surprisingly, mt-PA6-V also provides a greater maintenance of coronary blood flow and a faster time to reperfusion. Methods of treating thromboembolic disorders by the use of the diglycosylated form of t-PA derivatives that lack the Finger, Growth Factor and Kringle 1 domains, are disclosed by U.S. patent application Ser. No. 07/633,584, filed Dec. 24, 1990.

The present invention describes how these advantageous properties can be imparted to t-PA derivatives, such as mt-PA6, by means other than glycosylation. This is of importance because when these derivatives are produced by recombinant DNA technology from eukaryotic cell cultures, only 10%-25% of the resulting molecules are diglycosylated. The present invention makes it possible to convert the entire population of recombinantly produced t-PA derivatives that lack the Finger, Growth Factor and Kringle 1 domains to molecules having the enhanced thrombolytic properties of the diglycosylated form of the t-PA derivative molecule. Additionally, the economically disadvantageous process of separating the glycosylation forms in order to obtain only the diglycosylated form for use in in vivo thrombolytic therapy is avoided.

For the purposes of the present invention, as disclosed and claimed herein, the following terms are defined below.

Adduct—a combination of two or more independently stable compounds.

Amphipathic molecule—a molecule that has both polar and nonpolar portions, said nonpolar portion comprising a $C_9$—$C_{15}$ straight or branched chain alkyl group and said polar portion comprising an anionic group.

Glycoforms—forms of a glycoprotein with unique biological activities resulting from differences in the composition of the N-linked glycosylation of the protein.

Glycosylation—the attachment of oligosaccharides to a protein through an N-glycosidic bond with the Asparagine residue in an Asn-X-Ser/Thr sequence, wherein X is any amino acid except proline.

Reperfusion—restoration of blood flow caused by successful thrombolysis.

SUMMARY

The present invention provides adducts of human t-PA derivatives, wherein said adducts comprise a t-PA derivative that lacks the Finger, Growth Factor and Kringle 1 domains, bound to an amphipathic molecule. The invention also provides methods for preparing said adducts and compositions for the treatment of thromboembolic disorders.

DETAILED DESCRIPTION

The present invention provides adducts of the formula X:R—A, wherein X is a nonglycosylated or monoglycosylated t-PA derivative that lacks the Finger, Growth Factor, and Kringle 1 domains; R is a $C_9$ to $C_{15}$ straight or branched chain alkyl group; and A is an anionic group.

A preferred group of the above adducts comprises those adducts wherein R is a $C_{10}$ to $C_{14}$ straight or branched chain alkyl group and A is selected from the group comprising: sulfate; sulfonate; phosphate; phosphonate; or a carboxylate anion.

A more preferred group of the above adducts comprises adducts wherein R is a $C_{14}$ straight or branched chain alkyl group and A is selected from the group comprising: sulfate; sulfonate; phosphate; phosphonate; or a carboxylate anion.

An even more preferred group of the above adducts comprises adducts wherein R is a $C_{14}$ straight or branched chain alkyl group and A is sulfate.

Of the adducts listed above, the most preferred are those wherein X is mt-PA6. Thus, the most preferred adduct of the invention is wherein X is the t-PA derivative mt-PA6, R is a $C_{14}$ straight or branched chain alkyl group, and A is a sulfate group.

Examples of amphipathic compounds useful in the formation of the adducts of the invention are $C_9$–$C_{15}$ alkyl sulfates, phosphates, sulfonates, phosphonates and carboxylates such as the anionic forms of the nonylsulfate, decylphosphonate, dodecylsulfate, tetradecylcarboxylate, undecylsulfate, pentadecylphosphate, and like fatty acids in the anionic form. It should be noted that the anionic group may be bonded to the hydrocarbon chain at any position. It is possible that the hydrocarbon chain can contain olefinic bonds and may be substituted by two or more acidic groups in anionic form. Likewise, the anion portion A can be formed from one acid group of a dicarboxylic acid wherein the other carboxyl group forms an ester of a $C_9$–$C_{15}$ alcohol. For example, a dicarboxylic acid, such as malonic acid, succinic acid, glutaric acid, adipic acid, and the like, can form the half ester with an alkyl alcohol such as dodecyl alcohol or decyl alcohol to form the half acid ester. The latter is converted to the anionic form with a base, for example, sodium hydroxide or potassium hydroxide, to form the anionic salt form. The anionic charge of the anionic portion A will, of course, vary with the nature of the acid group. For example, the anionic portion A may bear a mono or dinegative charge.

The present invention also provides a method for preparing the adduct X:R—A which comprises mixing said t-PA derivative X, with a compound of the formula R—A under conditions that allow the binding of R—A to X, wherein R is a $C_9$ to $C_{15}$ straight or branched chain alkyl group and A is an anionic group.

A preferred embodiment of the above method is wherein R is a $C_{10}$ to $C_{14}$ straight or branched chain alkyl group and A is selected from the group comprising: sulfate; sulfonate; phosphate; phosphonate; or a carboxylate anion.

A more preferred embodiment of the above method is wherein R is a $C_{14}$ straight or branched chain alkyl group and A is selected from the group comprising: sulfate; sulfonate; phosphate; phosphonate; or a carboxylate anion.

An even more preferred embodiment of the above method is wherein R is a $C_{14}$ straight or branched chain alkyl group and A is sulfate.

Of the methods listed above, the most preferred are those wherein X is the t-PA derivative mt-PA6. Thus, the most preferred embodiment of the above methods is wherein X is the t-PA derivative mt-PA6, R is a $C_{14}$ straight or branched chain alkyl group, and A is a sulfate group.

Example 2 of the present invention demonstrates that the difference in enzymatic activity of the mono- and diglycosylated t-PA derivatives lacking the Finger, Growth Factor, and Kringle 1 domains is due to the presence of sialic acid residues at the terminus of the carbohydrate moieties on the t-PA derivative molecule. This is demonstrated by removal of these sialic acid residues with neuraminidase. When mt-PA6-V or mt-PA6-P was treated with neuraminidase, the specific activity of these molecules was converted to that of the nonglycosylated form of the mt-PA6. The nonglycosylated form of mt-PA6 can be obtained from an *Escherichia coli* host cell which is transformed with a recombinant DNA expression vector that enables expression of mt-PA6. *E. coli* is an organism that is incapable of producing glycosylated proteins.

The present invention provides that the contribution of the sialic acid residues to the fibrinolytic specific activity of the glycoforms of a t-PA derivative lacking the Finger, Growth Factor, and Kringle 1 domains can be duplicated by the addition of negative charge to this molecule. The t-PA molecule has several hydrophobic regions characterized by linear arrays of nonpolar amino acids. Because of this hydrophobicity, amphipathic molecules can be hydrophobically bound to a t-PA derivative, such as mt-PA6. The amphipathic molecules mimic the effect of the sialic acid residues on the fibrinolytic specific activity of the t-PA derivative molecule. When amphipathic molecules are added to a mixture of mt-PA6 glycoforms, the mixture is converted to a population of mt-PA6 molecules with the specific activity of the diglycosylated mt-PA6-V molecule.

The effect of the amphipathic molecules on the specific activity of mt-PA6 was found to be dependent on the size of the alkyl group. For example, amphipathic molecules such as $C_8$, $C_{10}$, $C_{12}$, $C_{14}$, $C_{16}$, and $C_{18}$ alkyl sulfates were bound to the mt-PA6 molecules. The addition of $C_{14}$ alkyl sulfate had the maximum effect of the fibrinolytic specific activity of mt-PA6-P. The binding of the $C_{14}$ alkyl sulfate to mt-PA6-P changed the specific activity of the molecule to the level of mt-PA6-V. The $C_8$, $C_{16}$ and $C_{18}$ alkyl sulfates did not have this effect. The results of this analysis are presented in Table 1 of Example 3.

The effect of these alkyl sulfates is due to the sulfate group because tetradecanol, which does not contain an anionic group, had no effect on the specific activity of mt-PA6-P. Additionally, binding of the $C_{14}$ alkyl sulfate to neuraminidase-treated mt-PA6-P restores the fibrinolytic specific activity to the same value as that observed for mt-PA6-V. Binding studies with radiolabelled $C_{14}$ alkyl sulfate and mt-PA6-P or mt-PA6-V demonstrated that one mole of $C_{14}$ alkyl sulfate is bound per mole of mt-PA6. These results demonstrate that when amphipathic molecules are bound to neuraminidase-treated or monoglycosylated forms of a t-PA derivative that lacks the Finger, Growth Factor, and Kringle 1 domain, the activity of these t-PA derivatives is converted to that of the diglycosylated form of the molecule.

The skilled artisan will recognize that the conditions for the binding of the t-PA derivative X, to the amphipathic compound R—A, as listed in Example 3, are merely illustrative. Conditions which optimize the binding of the t-PA derivative to the amphipathic compound should be chosen. Conditions such as temperature, pH, and the molar ratio of the t-PA derivative to the amphipathic compound, for example, may be varied in order to optimize the formation of the X:R—A adduct.

The present invention is also useful in converting t-PA derivatives that lack the Finger, Growth Factor and Kringle 1 domains, which are expressed and purified from prokaryotic host cells, such as *Escherichia coli*, to forms which have the properties of the diglycosylated form of the molecule. The present invention is especially useful in this setting because prokaryotic host cells, such as *E. coli*, are incapable of glycosylating proteins. Thus, the present invention provides a method for imparting the biological activity of the diglycosylated form of this t-PA derivative to a derivative obtained from a host cell incapable of glycosylating proteins.

The skilled artisan will recognize that the present invention is applicable to t-PA derivatives that lack the Finger, Growth Factor and Kringle 1 domains. mt-PA6 is illustrative of such a t-PA derivative and is used herein to exemplify the usefulness of the present invention.

The effectiveness of a particular amphipathic molecule in the method of the present invention may be measured by techniques set out in the Examples below. Amphipathic molecules may be bound to the t-PA derivative by the method described in Example 3. The specific activity of these molecules is then measured by the method of Example 1. If further analysis is desired, these compounds may be analyzed by the methods described by Jackson et al., supra.

The adducts of the present invention will be useful in the treatment of a variety of thromboembolic disorders. Such disorders include deep vein thrombosis, disseminated intravascular coagulation, emboli originating from the heart or peripheral arteries, acute myocardial infarction, thrombotic strokes, and fibrin deposits associated with invasive cancers. Thromboembolic disorders can be treated by administration of a thrombolytically effective dose of an adduct, X:R—A, of the present invention. The present invention thus provides a method for treating thromboembolic disorders in mammals which comprises administering to said mammal a thrombolytically effective dose of a t-PA adduct presented by the formula X:R—A.

The adducts of the present invention can be formulated according to known methods to prepare pharmaceutically useful compositions, whereby an adduct of the present invention is combined in admixture with a pharmaceutically acceptable carrier vehicle. Suitable carrier vehicles and their formulation, inclusive of other human proteins, e.g., human serum albumin, are described for example, in *Remington's Pharmaceutical Sciences* 16th ed., 1980, Mack Publishing Co., edited by Oslo et al.. Such compositions will contain an effective amount of an adduct of the present invention together with a suitable amount of carrier vehicle to prepare pharmaceutical compositions suitable for effective administration to the host. Such compositions can be administered parentally, or by other means that ensure its delivery to the bloodstream in an effective form. The preferred method of administration of an adduct of the present invention is by bolus intravenous administration. Preferred dosages range from about 0.01 mg/kg to about 10 mg/kg. More preferred dosages range from about 0.1 mg/kg to about 1 mg/kg. The most preferred dosage is about 0.4 mg/kg.

The following examples are intended to assist in further understanding of the invention. Particular materials employed, species and conditions are intended to be further illustrative of the invention and not limiting the reasonable scope thereof.

EXAMPLE 1

In Vitro Activity of mt-PA6 mt-PA6 can be produced and isolated in accordance with the methods described by Burck et al., supra. Fibrinolytic activity of the glycoforms of mt-PA6 was determined by a radial diffusion assay on a fibrin-agarose matrix plate (Schumacher and Schill, 1972, *Anal. Biochem.* 48:9–26). Small wells (6.5 mm) were cut into the fibrin-agarose matrix plate for sample application. Samples (20 μl) containing either mt-PA6 or reference standard t-PA, WHO Standard, batch 83/517 (Gaffey and Curtis, 1985, *Thromb. Haemostasis* 53: 134–136), were placed in the precut wells of the plate. The plates were then incubated at 37° C. in a moist oven for 16 hours. Activity values (IU) were assigned to mt-PA6 samples by comparison of the areas of the clear lysis zones caused by the mt-PA6 samples to a standard curve of clear lysis zones of the t-PA standard plotted against the log of the t-PA concentration (3.75–15.0 IU/ml). The protein content of mt-PA6 was determined using a computer-generated extinction coefficient (1.691 for a 1 mg/ml solution at 278 nm) derived from amino acid content of the enzyme.

EXAMPLE 2

Neuraminidase Treatment of mt-PA6

To determine the effect of the removal of the negatively charged sialic acid residues from the carbohydrate moieties of mt-PA6, samples of mt-PA6-P and mt-PA6-V were treated with neuraminidase (Boehringer Mannheim, Indianapolis, Ind.) as follows. A 1.0 mg/ml (25 μM) solution of either mt-PA6-P or mt-PA6-V was dissolved in 5.0 ml of 0.05M sodium acetate, pH 5.0. Next, 0.24 ml of a 1 IU/ml solution of neuraminidase was added and the reaction mixture was incubated at 37° C. The progress of the reaction was monitored by chromatography of aliquots of the reaction mixture using a MONO S column on a Pharmacia FPLC system (800 Centennial Avenue, Piscataway, N.J. 08854). As the negatively charged sialic acid residues are removed from either mt-PA6-P or mt-PA6-V by the neuraminidase treatment, a later eluting (more positive) peak of mt-PA6 appears.

The fibrinolytic specific activity of mt-PA6-P (1,300,000 IU/mg) and mt-PA6-V (780,000 IU/mg) is increased to 1,870,000 IU/mg and 1,810,000 IU/mg, respectively, by the removal of the sialic residues by neuraminidase. These specific activities are approximately the same as that observed for the non-glycosylated form of mt-PA6 expressed in *Escherichia coli*.

EXAMPLE 3

Treatment of mt-PA6 with Alkyl Sulfates

To determine the effect of incubation of amphipathic molecules on the fibrinolytic specific activity of mt-PA6, mt-PA6-P was incubated with straight chain $C_8$, $C_{12}$, $C_{14}$ and $C_{16}$ alkyl sulfates. Tetradecanol was used as a control. The alkyl sulfates used in the exemplification of the present invention were prepared as described by Sobel et al., 1941, *J. Am. Chem Soc.* 63:1259–1261.

Five mls of a 1 mg/ml solution of mt-PA6-P in 0.001N HCl and 0.001% Tween 80 was incubated with a 10-fold molar excess (0.25 mM) of one of the above alkyl sulfates or control for 16 to 18 hours at 5° C. The solution was then dialyzed at 5° C. against five changes of 500 ml of 0.001N HCl and 0.001% Tween 80 to remove excess alkyl sulfate or tetradecanol not bound to mt-PA6-P. Fibrinolytic activity of these molecules was determined by the method described in Example 1. These fibrinolytic activities are shown in Table 1.

TABLE 1

| Sample | Fibrinolytic Specific Activity |
| --- | --- |
| mt-PA6-P | 1,300,000 IU/mg |
| mt-PA6-P + $C_8$ alkyl sulfate | 1,310,000 IU/mg |
| mt-PA6-P + $C_{12}$ alkyl sulfate | 850,000 IU/mg |
| mt-PA6-P + $C_{14}$ alkyl sulfate | 654,000 IU/mg |
| mt-PA6-P + $C_{16}$ alkyl sulfate | 1,300,000 IU/mg |
| mt-PA6-P + tetradecanol | 1,320,000 IU/mg |

The data of Table 1 demonstrate that the introduction of negative charge by these amphiphatic molecules has a profound effect in the fibrinolytic specific activity of the mt-PA6 molecule. The specific activity of the mt-PA6:$C_{14}$ sulfate adduct is the same as that of mt-PA6-V. The mt-PA6 adduct may be isolated and purified by chromatography according to the method of Burck et al., supra, to separate the mt-PA6:C14 sulfate adduct from the excess $C_{14}$ sulfate in the reaction mixture.

EXAMPLE 4

Treatment of mt-PA6 with Neuraminidase and Tetradecyl Sodium Sulfate

To determine the effect of incubation of amphiphathic molecules on the fibrinolytic activity of neuraminidase-treated mt-PA6, the mt-PA6-P or mt-PA6-V molecules were treated with neuraminidase, as described in Example 2, to remove the sialic acid residues from the mt-PA6 molecules. Each mt-PA6/-neuraminidase reaction mixture was then adjusted to pH 3.0 with HCl, and a 10-fold molar excess (25 mM) of tetradecyl sodium sulfate was added. Each reaction mixture was then incubated at 5° C. for 16–18 hours and was then dialyzed against five changes of 500 ml of 0.001N HCl and 0.001% Tween 80 to remove excess tetradecyl sodium sulfate not bound to the neuraminidase-treated mt-PA6. Specific activities were measured by the method of Example 1. The specific activity of mt-PA6-P and mt-PA6-V after treatment with neuraminidase was 1,870,000 IU/mg and 1,810,000 IU/mg, respectively. After incubation with tetradecyl sodium sulfate, the fibrinolytic specific activity decreased to 650,000 IU/mg and 710,000 IU/mg, respectively. Thus, the specific activity of each of the neuraminidase-treated mt-PA6 molecules incubated with tetradecyl sodium sulfate was approximately the same as that of the diglycosylated mt-PA6-V.

EXAMPLE 5

Stoichiometry of Binding Tetradecyl Sodium Sulfate and mt-PA6

To investigate the stoichiometry of the amphipathic molecules binding to mt-PA6, mt-PA6-P and mt-PA6-V were incubated with a 10-fold molar excess of tritium-labelled tetradecyl sodium sulfate (NEN Research Products, Boston, Mass.) using the methodology described in Example 3. After extensive dialysis (by the method of Example 4) to remove any excess radiolabelled tetradecyl sodium sulfate not bound to the mt-PA6, the concentration of the mt-PA6 in the dialyzed sample was determined using the calculated extinction coefficient for mt-PA6. The concentration of tritium-labelled tetradecyl sodium sulfate bound to mt-PA6 was determined by calculations based on scintillation counting and the known specific activity of the tritium-labelled alkyl sulfate. For both mt-PA6-P and mt-PA6-V, one mole of tetradecyl sodium sulfate bound per mole of enzyme.

We claim:

1. An adduct of the formula X:R−A, wherein X is a nonglycosylated or monoglycosylated t-PA derivative that lacks the Finger, Growth Factor, and Kringle 1 domains; R is a $C_9$ to $C_{15}$ straight or branched chain alkyl group; and A is an anionic group.

2. An adduct of claim 1 wherein R is a $C_{10}$ to $C_{14}$ straight or branched chain alkyl group.

3. An adduct of claim 2 wherein R is a $C_{14}$ straight or branched chain alkyl group.

4. An adduct of claim 1 wherein A is selected from the group consisting of: sulfate; sulfonate; phosphate; phosphonate; and a carboxylate anion.

5. An adduct of claim 2 wherein A is selected from the group consisting of: sulfate; sulfonate; phosphate; phosphonate; and a carboxylate anion.

6. An adduct of claim 3 wherein A is sulfate.

7. An adduct of claim 1 wherein X is mt-PA6.

8. An adduct of claim 2 wherein X is mt-PA6.

9. An adduct of claim 3 wherein X is mt-PA6.

10. An adduct of claim 4 wherein X is mt-PA6.

11. An adduct of claim 5 wherein X is mt-PA6.

12. An adduct of claim 6 wherein X is mt-PA6.

13. A method for preparing the adduct of claim 1 which comprises incubating said t-PA derivative X, with a compound of the formula R−A for about 16–18 hours at about 5° C. to allow the binding of R−A to X, wherein R is a $C_9$ to $C_{15}$ straight or branched chain alkyl group and A is an anionic group.

14. A method of claim 13 wherein R is a $C_{10}$ to $C_{14}$ straight or branched chain alkyl group.

15. A method of claim 13 wherein R is a $C_{14}$ straight or branched chain alkyl group.

16. A method of claim 13 wherein A is selected from the group consisting of: sulfate; sulfonate; phosphate; phosphonate; and a carboxylate anion.

17. A method of claim 14 wherein A is selected from the group consisting of: sulfate; sulfonate; phosphate; phosphonate; and a carboxylate anion.

18. A method of claim 15 wherein A is sulfate.

19. The method of claim 13 wherein X is mt-PA6.

20. The method of claim 14 wherein X is mt-PA6.

21. The method of claim 15 wherein X is mt-PA6.

22. The method of claim 16 wherein X is mt-PA6.

23. The method of claim 17 wherein X is mt-PA6.

24. The method of claim 18 wherein X is mt-PA6.

25. A method of treating thromboembolic disorders by administration of a thrombolytically effective dose of the t-PA adduct of claim 1 to a patient in need thereof.

26. A method of treating thromboembolic disorders by administration of a thrombolytically effective dose of the t-PA adduct of claim 7 to a patient in need thereof.

27. A method of treating thromboembolic disorders by administration of a thrombolytically effective dose of the t-PA adduct of claim 12 to a patient in need thereof.

28. A method of claim 25 wherein the dose of said t-PA derivative is about 0.01 mg/kg to about 10 mg/kg.

29. A method of claim 26 wherein the dose of said t-PA adduct is about 0.01 mg/kg to about 10 mg/kg.

30. A method of claim 27 wherein the dose of said t-PA adduct is about 0.01 mg/kg to about 10 mg/kg.

31. A method of claim 28 wherein the dose of said t-PA adduct is about 0.01 mg/kg to about 1 mg/kg.

32. A method of claim 29 wherein the dose of said t-PA adduct is about 0.01 mg/kg to about 1 mg/kg.

33. A method of claim 30 wherein the dose of said t-PA adduct is about 0.01 mg/kg to about 1 mg/kg.

34. The method of claim 31 wherein the dose of said t-PA adduct is about 0.4 mg/kg.

35. The method of claim 32 wherein the dose of said t-PA adduct is about 0.4 mg/kg.

36. The method of claim 33 wherein the dose of said t-PA adduct is about 0.4 mg/kg.

37. A composition comprising a thrombolytically effective dose of the adduct of claim 1 in admixture with a pharmaceutically acceptable carrier.

38. A composition comprising a thrombolytically effective dose of the adduct of claim 7 in admixture with a pharmaceutically acceptable carrier.

39. A composition comprising a thrombolytically effective dose of the adduct of claim 12 in admixture with a pharmaceutically acceptable carrier.

* * * * *